(12) United States Patent
Ovsyanko

(10) Patent No.: US 9,207,210 B2
(45) Date of Patent: Dec. 8, 2015

(54) METHOD AND A DEVICE FOR ATTRACTING MAGNETIC PARTICLES TO A SURFACE

(75) Inventor: Mikhail Mikhaylovich Ovsyanko, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 142 days.

(21) Appl. No.: 13/821,022

(22) PCT Filed: Sep. 7, 2011

(86) PCT No.: PCT/IB2011/053910
§ 371 (c)(1),
(2), (4) Date: Mar. 6, 2013

(87) PCT Pub. No.: WO2012/032476
PCT Pub. Date: Mar. 15, 2012

(65) Prior Publication Data
US 2013/0163140 A1 Jun. 27, 2013

(30) Foreign Application Priority Data
Sep. 9, 2010 (EP) .................................... 10175953

(51) Int. Cl.
| G01N 27/74 | (2006.01) |
| H01F 7/06 | (2006.01) |
| G01N 33/543 | (2006.01) |
| G01R 33/12 | (2006.01) |
| G01N 21/552 | (2014.01) |
| G01N 35/00 | (2006.01) |

(52) U.S. Cl.
CPC ........ *G01N 27/745* (2013.01); *G01N 33/54366* (2013.01); *G01R 33/1269* (2013.01); *H01F 7/064* (2013.01); *G01N 21/552* (2013.01); *G01N 35/0098* (2013.01)

(58) Field of Classification Search
USPC ......................................... 361/143, 144, 145
See application file for complete search history.

(56) References Cited

U.S. PATENT DOCUMENTS

| 7,253,999 | B2* | 8/2007 | Ker et al. ......................... 361/56 |
| 7,408,752 | B2* | 8/2008 | Ma et al. .......................... 361/56 |
| 7,663,853 | B2* | 2/2010 | Ker et al. ...................... 361/93.1 |
| 8,411,274 | B2* | 4/2013 | Verschuren et al. ........... 356/445 |
| 2003/0222703 | A1* | 12/2003 | Ker et al. ........................ 327/379 |
| 2007/0188952 | A1* | 8/2007 | Ker et al. ......................... 361/56 |
| 2008/0151457 | A1* | 6/2008 | Apfel ............................. 361/111 |
| 2008/0191688 | A1 | 8/2008 | Kahlman et al. |
| 2008/0246345 | A1* | 10/2008 | Zecri et al. ..................... 307/413 |
| 2009/0116157 | A1* | 5/2009 | Besse et al. ..................... 361/56 |
| 2009/0180244 | A1* | 7/2009 | Kiyohara .................. 361/679.01 |

(Continued)

FOREIGN PATENT DOCUMENTS

| WO | 2005010542 A2 | 2/2005 |
| WO | 2005010543 A1 | 2/2005 |

(Continued)

*Primary Examiner* — Thienvu Tran
*Assistant Examiner* — Angela Brooks

(57) ABSTRACT

Magnetic particles (1) are attracted to a contact surface (11) in an associated sensor device (100) by generating a pulsed magnetic field (B) according to an actuation protocol. The protocol includes a "local attraction phase" during which the duty cycle of the pulsations is smaller than about 10%, preferably ranging between 2% and 5%. These small duty cycles are advantageous in bringing magnetic particles (1) into actual contact with the contact surface (11).

20 Claims, 2 Drawing Sheets

(56) References Cited

U.S. PATENT DOCUMENTS

| | | | |
|---|---|---|---|
| 2010/0128402 A1* | 5/2010 | Besse et al. | 361/56 |
| 2010/0165345 A1* | 7/2010 | Bruls et al. | 356/436 |
| 2010/0188076 A1* | 7/2010 | Kahlman et al. | 324/232 |
| 2010/0324828 A1* | 12/2010 | Kahlman et al. | 702/19 |
| 2011/0084339 A1* | 4/2011 | Besse et al. | 257/362 |
| 2011/0244596 A1* | 10/2011 | Evers et al. | 436/518 |
| 2011/0279114 A1* | 11/2011 | Van Zon et al. | 324/244.1 |
| 2012/0236445 A1* | 9/2012 | Ker et al. | 361/56 |
| 2012/0258553 A1* | 10/2012 | Dittmer et al. | 436/501 |
| 2013/0088221 A1* | 4/2013 | Van Zon et al. | 324/228 |
| 2013/0170089 A1* | 7/2013 | Ovsyanko | 361/143 |
| 2015/0187479 A1* | 7/2015 | Van Lieshout et al. | 335/306 |

FOREIGN PATENT DOCUMENTS

| | | |
|---|---|---|
| WO | 2008102218 A1 | 8/2008 |
| WO | 2008155716 A1 | 12/2008 |
| WO | 2010084383 A1 | 7/2010 |

\* cited by examiner

METHOD AND A DEVICE FOR ATTRACTING MAGNETIC PARTICLES TO A SURFACE

FIELD OF THE INVENTION

The invention relates to a method for attracting magnetic particles to a contact surface by magnetic fields. Moreover, it relates to a sensor device in which magnetic particles are attracted to a contact surface.

BACKGROUND OF THE INVENTION

From the US 2011/0279114, a method and a sensor device are known in which magnetic particles are attracted to a sensor surface by the application of pulsed magnetic fields. Chains of magnetic particles that form at the sensor surface during the "on" times of the magnetic field can break up during the "off" times of the field, thus allowing also remote particles of the chains to reach the surface by diffusion.

SUMMARY OF THE INVENTION

In view of this background, it was an object of the present invention to provide means for an improved processing of magnetic particles, particularly an improved attraction of magnetic particles to a surface.

According to a first aspect, a method is provided for attracting magnetic particles to a surface, which will be called "contact surface" in the following, by generating a pulsed magnetic field according to a given actuation protocol. The term "magnetic particles" shall comprise both permanently magnetic particles as well as magnetizable particles, for example superparamagnetic beads. The size of the magnetic particles typically ranges between 3 nm and 50 µm. Moreover, the magnetic particles may comprise bound target components one is actually interested in. The "contact surface" will typically be the interface between the material of some container or cartridge and a hollow sample chamber in which a sample with magnetic particles can be provided. Moreover, the expression "pulsed magnetic field" shall refer to a magnetic field that is repetitively switched between two different states, particularly two different field strengths. Most preferably, one of these field strengths is zero, i.e. the pulsed magnetic field is repetitively switched "on" and "off".

The actuation protocol that determines the temporal pulsation schedule of the magnetic field shall include a phase which is called "local attraction phase" in the following, wherein the duty cycle is smaller than about 10% during this local attraction phase. Preferably, the duty cycle during the local attraction phase is smaller than about 9%, more preferably smaller than about 7%, and most preferably smaller than about 6%. As usual, the term "duty cycle" shall denote the ratio between the duration for which the field is in a first state to the total duration of one period of pulsation. In case of a magnetic field that is switched "on" for a duration $t_{ON}$ and then switched "off" for a duration $t_{OFF}$, the duty cycle DC is typically defined as $$DC = \frac{t_{ON}}{t_{ON} + t_{OFF}}.$$

According to a second aspect, a sensor device for the detection of magnetic particles at a contact surface comprises the following components:

a) A magnetic field generator for generating a magnetic field that attracts magnetic particles to the contact surface.

b) A control unit for controlling the magnetic field generator in a pulsed operation according to an actuation protocol, wherein said actuation protocol comprises a local attraction phase during which the duty cycle of the pulsations is smaller than about 10%.

As a method of the kind described above can be executed by the sensor device, reference is made to the above description of said method for more information about the details of the sensor device.

The described method and the sensor device apply an attraction of magnetic particles to a contact surface by a pulsed magnetic field with a extraordinarily short duty cycle of less than 10%. In other words, the attraction of the magnetic particles is achieved during a local attraction phase by switching the magnetic field off for more than about 90% of the time. Surprisingly, this at first glance paradoxical approach turns out to be very efficient in bringing magnetic particles actually into contact with the contact surface.

In the following, various preferred embodiments will be described that relate both to the method and the sensor device described above.

According to a first particular embodiment, the duty cycle ranges during the local attraction phase between about 2% and about 5%. Magnetic attraction is then achieved by very short, spike-like pulsations of the magnetic field.

In another embodiment, the actuation protocol comprises a further phase, called "global attraction phase", during which the duty cycle of the pulsations of the magnetic field is larger than about 25%, preferably larger than about 40%. The times during which the magnetic field is "on" are hence approximately of the same order of magnitude as the times during which it is "off", i.e. the effects of magnetically forced attraction and free diffusion on the migration of the magnetic particles are comparable on a temporal scale. The prolonged effect of the magnetic attraction enhances particularly the migration of magnetic particles that are still farther away from the contact surface and not yet affected by the formation of clusters. As the effects of the magnetic field are hence predominant in the bulk of the sample at hand, the corresponding phase of the actuation protocol has been called "global attraction phase".

Most preferably, the aforementioned global attraction phase precedes the local attraction phase. The global attraction phase can then be used to concentrate magnetic particles from within the whole sample volume at the contact surface, while the subsequent local attraction phase is optimized with respect to bringing the collected magnetic particles into actual contact with the contact surface.

The frequency of the pulsation of the magnetic field ranges during the local attraction phase preferably between about 0.2 Hz and about 10 Hz, most preferably between about 1 Hz and 4 Hz. The frequency f determines how fast the periods of the pulsation are repeated. With the notation introduced above, it can be expressed as $$f = 1/(t_{ON} + t_{OFF})$$

In practice, a frequency that yields optimal results is usually determined in dependence on various process parameters, for example the size of the magnetic particles.

The contact surface to which the magnetic particles are attracted may optionally comprise binding sites for said magnetic particles, such that they can permanently be immobilized at the contact surface. To achieve high binding rates, it is important that the magnetic particles actually come into contact with the contact surface, which is favorably achieved by the actuation protocol described above.

In general, the magnetic particles may be attracted to the contact surface (and optionally be bound there) for various reasons, for example in order to purify a sample. In an important application, the magnetic particles are detected at the contact surface during and/or after the execution of the magnetic actuation protocol. Such a detection may particularly be done in combination with the aforementioned binding of magnetic particles, wherein said binding is typically specific with respect to different types of magnetic particles (the binding may e.g. be specific with respect to certain target molecules of a sample that are labeled with magnetic beads).

In the aforementioned embodiment, the detection of the magnetic particles at the contact surface may optionally be achieved with an optical, magnetic, mechanical, acoustic, thermal and/or electrical sensor element. A magnetic sensor element may particularly comprise a coil, Hall sensor, planar Hall sensor, flux gate sensor, SQUID (Superconducting Quantum Interference Device), magnetic resonance sensor, magneto-restrictive sensor, or magneto-resistive sensor of the kind described in the US 2008/0309329 or US 2006/0194327, especially a GMR (Giant Magneto Resistance), a TMR (Tunnel Magneto Resistance), or an AMR (Anisotropic Magneto Resistance). An optical sensor element may particularly be adapted to detect variations in an output light beam that arise from a frustrated total internal reflection (FTIR) due to magnetic particles at a sensing surface (cf. WO 2008/155716).

The described method will typically be realized with the help of a computing device, e.g. a microprocessor or an FPGA in the control unit of the sensor device. Accordingly, the present invention further includes a computer program product which provides the functionality of any of the methods according to the present invention when executed on a computing device.

Further, the present invention includes a data carrier, for example a floppy disk, a hard disk, an EPROM, or a compact disc (CD-ROM), which stores the computer product in a machine readable form and which executes at least one of the methods of the invention when the program stored on the data carrier is executed on a computing device. The data carrier may particularly be suited for storing the program of the computing device mentioned in the previous paragraph.

Nowadays, such software is often offered on the Internet or a company Intranet for download, hence the present invention also includes transmitting the computer product according to the present invention over a local or wide area network.

The invention further relates to the use of the sensor device described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

DESCRIPTION OF PREFERRED EMBODIMENTS

In the following, the invention will be described with respect to a biosensor for the detection of magnetic particles, particularly the optical detection using frustrated total internal reflection (FTIR).

One of the main advantages of using magnetic particles in a biological assay is that they can be actuated, which helps to decrease the time needed to perform the assay. In one format, the magnetic particles are actuated to a sensor surface, where the number of nanoparticles that bind to the surface is dependent on the concentration of an analyte. For a fast and efficient assay, the contact between the particles and the sensor surface has to be maximized to allow biological bonds to be formed. To obtain a high surface contact in a short time, external magnets may be used to attract the particles to the sensor surface. Due to the magnetic attraction, the number of magnetic beads (particles) near the sensitive surface increases, and the sensor signal increases accordingly.

Figure 1:
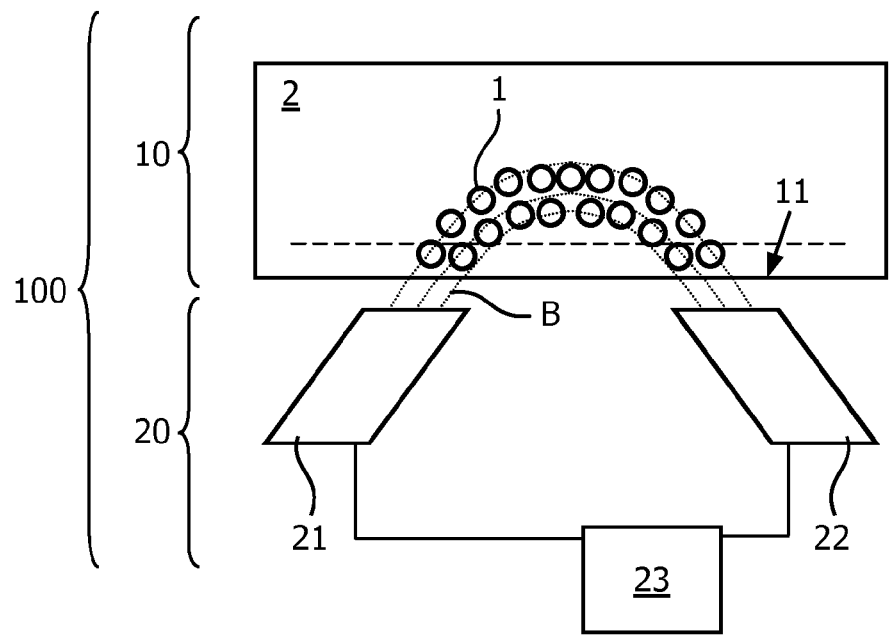
FIG. 1 schematically shows the formation of clusters of magnetic particles at a contact surface during the "on" phase of a pulsed magnetic field.
Figure 2:
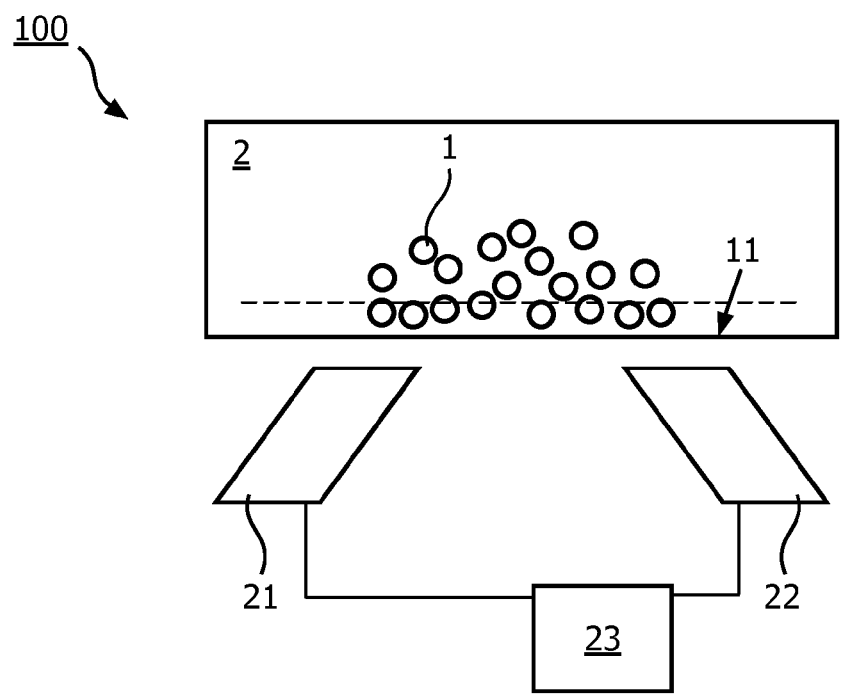
FIG. 2 shows the diffusion of the magnetic particles of FIG. 1 during the "off" phase of the pulsed magnetic field.

FIGS. 1 and 2 illustrate the situation at the contact surface 11 of a sensor device 100. The sensor device 100 comprises a (typically exchangeable/disposable) container or cartridge 10 with a sample chamber 2 in which magnetic particles 1 are provided above said contact surface 11. Moreover, the sensor device 100 comprises a readout unit 20 with magnets 21, 22 for generating a magnetic field B in the sample chamber and with a detection unit (not shown) for detecting magnetic particles at the contact surface 11. The detection unit may for instance comprise a light source and a light detector for measuring frustrated total internal reflection (FTIR) of a light beam at the contact surface 11. The magnets 21, 22 are operated by a control unit 23 according to some given actuation protocol.

In a real assay, a pulsed magnetic attraction schedule is often used to attract magnetic particles 1 to the contact surface 11. In such a scheme, the magnetic field B is periodically switched on and off. When the magnetic field is on, beads are attracted towards the surface 11. When the magnetic field is switched off, beads will diffuse towards the surface or away from the surface, depending of their original position. More details about the application of a pulsed magnetic field may be found in the WO 2010/084383 A1, which is incorporated into the present application by reference.

Experiments indicate that the number of magnetic particles that come in contact with the contact surface is far from optimal when the magnet is switched on, degrading the performance of the assay. When the magnet is switched off, the immediate decrease in signal that follows indicates that many particles were close to, but not in contact with the surface. One explanation for this phenomenon could be that the magnetic field lines to which the strings of particles align are not perfectly parallel to the sensor surface, as observed in simulations of the magnetic field and indicated in the schematic illustration of FIG. 1. In the magnetic field B of the magnet 21, 22, the magnetic particles 1 form large strings or chains along the field lines. As a result, fewer particles are close enough to the contact surface 11 to be detected (the boundary of detection is indicated by a dashed line in FIGS. 1 and 2).

FIG. 2 illustrates the situation when the magnet 21, 22 is switched off. Now the magnetic particles 1 can diffuse to the contact surface 11.

In view of the above, a method is proposed here to increase the biosensor signal by using a new actuation protocol. With this new actuation protocol, current hardware configurations can still be used.

In the following, it will first be explained why a pulsed actuation protocol works better than a continuous magnetic actuation protocol under the condition that both methods consume the same amount of energy. On first thought one would expect that continuous magnetic attraction is better than pulsed actuation because during a larger amount of time the magnetic beads are attracted towards the surface. This is only partially true. Indeed more magnetic beads are collected near the surface in the same amount of time by continuous attraction. However, from experiments it has been shown that only a small fraction of the particles which are collected near the surface will actually be able to reach and bind to the surface. This is caused by the magnetic bead-bead interaction. As soon as the surface is covered with a certain amount of beads (e.g. approximately 10% at the center but even lower near the poletips of the magnets), beads approaching the surface will be attracted by the beads which are already present on the surface due to the magnetic actuation force. This process is known as "magnetic clustering". Because the magnetic field makes an angle with the surface, the clustered beads will be outside the detection region (cf. FIG. 1). So, although these beads are attracted by the magnetic field, they will not make contact with the surface and therefore cannot bind to the surface. Only when the magnetic field is switched off, the clustered beads will be released and by diffusion are able to make contact with the surface (cf. FIG. 2). When the magnetic field is continuously switched on, the clustered beads will never come into contact with the surface and the signal remains low (typically only 3-10% of the available 100% signal). Therefore, for a pulsed actuation protocol both the attraction time ($t_{ON}$) as well as the time that the magnetic field is switched off ($t_{OFF}$) are important. During the attraction time the beads are transported to a region near the surface where the concentration of beads increases. During the time the magnetic field is off, the beads can actually reach the surface through diffusion and bind. The ratio $t_{ON}/(t_{ON}+t_{OFF})$ is called the "duty-cycle" (DC) of the actuation protocol. To achieve quickly a large signal, the number of beads transported to a region near the surface during the ON-phase should match the number of beads transported to the surface by means of diffusion during the OFF-phase. This can be equated as follows:

$$R_{ON} \cdot t_{ON} = R_{OFF} \cdot t_{OFF}$$

where $R_{ON}$ and $R_{OFF}$ are respectively the transport rates (expressed in beads/sec) during the ON and OFF phase, i.e. the transport rates during magnetic attraction and diffusion. The optimum duty-cycle of the pulsed signal can therefore be expressed in the transport rates:

$$\frac{R_{OFF}}{R_{ON} + R_{OFF}} = DC$$

The duty cycle indicates the percentage of time that the actuation field is ON. This equation shows that the duty-cycle of the pulsed actuation signal is important and has to be optimized given the transport rates of the system.

When the magnet is switched on, the unbound particles are immediately pulled back from the surface, supposedly to form the large strings as it is shown in FIG. 1. From these measurements it can be concluded that only a very short pulse of the magnet is needed to form the strings and that a longer pulse does not contribute much to the surface contact of the particles. In other words, the duty cycle must have a certain amplitude and duration sufficient to attract the magnetic particles and reduce the time which the particles spend in the string. Furthermore, this pulse has to be succeeded by a long "off" time tailored to the specific situation, i.e. the distance that has to be spanned and the size of the used particles. A last consideration that has to be taken into account is that the chance that a bond is formed is not only dependent by the amount of particles that come in contact with the surface, but also the number of times the whole process is repeated.

Figure 3:
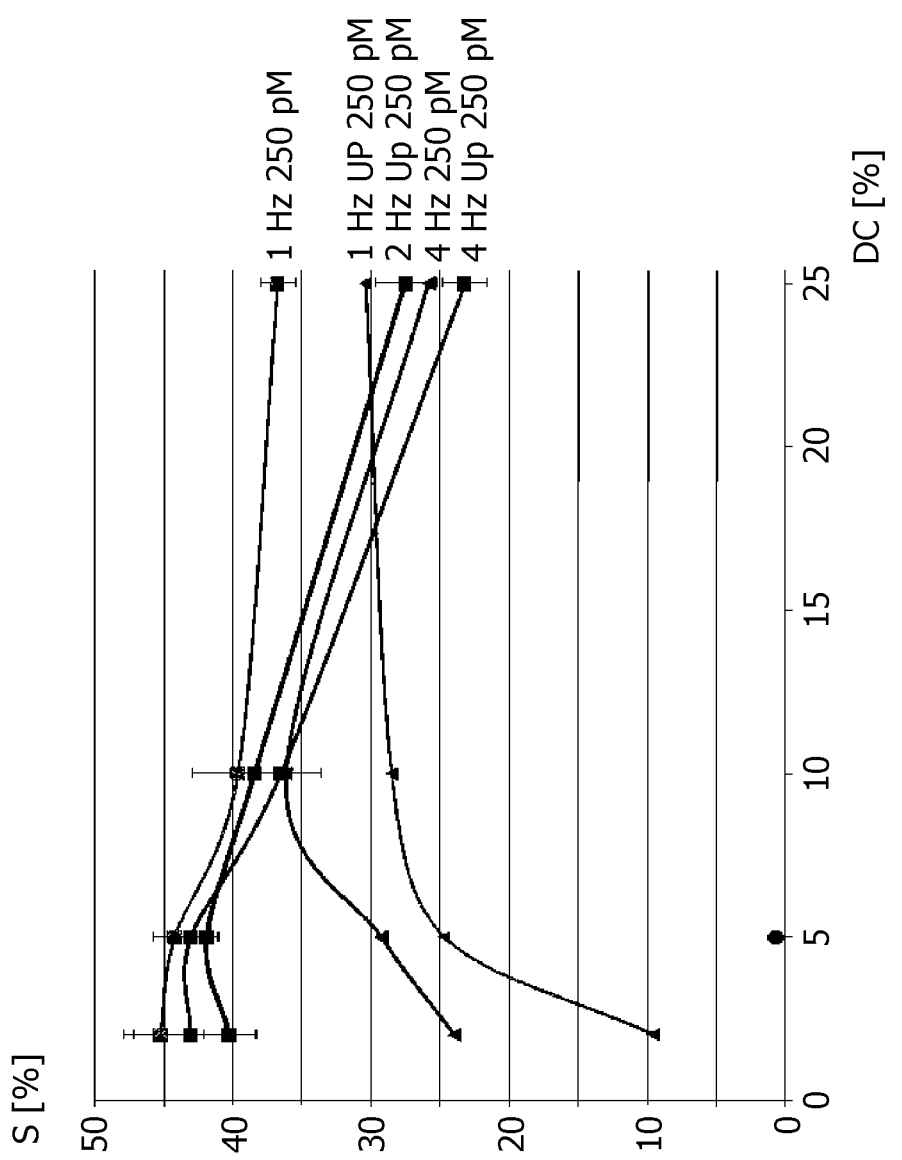
FIG. 3 is a diagram representing FTIR measurement signals (vertical axis, relative units) in dependence on the duty cycle (horizontal axis) of a pulsed magnetic field for different frequencies of the pulsation.

Experimental data show that the total signal change (e.g. of the FTIR measurement signal obtained with the sensor device 100 of FIGS. 1, 2) slightly depends on the frequency f of the actuation. FIG. 3 illustrates the influence of the duty-cycle (DC) and how it can be optimized. The diagram shows experimental results that were performed in human plasma with troponin concentration of 250 pM. An index "Up" at a curve means that an Up-concentration step (global attraction phase) was used in this experiment. For low (2-5%) DCs the process is diffusion-limited, but a high signal level can be obtained. The low DC approach is not possible for an up-concentration step, as beads have not enough time to reach the contact surface. Therefore, the actuation protocol is preferably split in two parts. The goal of the first part is the up-concentration of the magnetic beads near the contact surface. For this "global attraction phase" a high DC is used, for example a DC of about 50%. In experiments, the concentration speed was optimal for high levels of the DC, and it was possible to attract almost all beads from the volume of a sample chamber with a height of 100 μm within 3-5 seconds.

The following table represents an exemplary actuation protocol for a troponin assay:

| Actuation Set | Actuation Set Cycles | f [HZ] | DC [%] |
|---|---|---|---|
| Calibration step | 5 | | |
| Incubation step (target molecules capturing) | 90 | 2 | 20 |
| Up-concentration step (attraction towards sensitive surface) | 5 | 5 | 50 |
| Binding step (formation of molecular "sandwich") | 195 | 2 | 5 |
| Washing step (removes unbound nanoparticles) | 10 | | |

"Actuation Set Cycles" = duration of specific step of the actuation protocol in seconds
"f" = pulsation frequency of the magnetic actuation field
"DC" = duty cycle of the magnetic actuation field In summary, a magnetic actuation protocol using a low duty cycle (DC) is proposed. The actuation protocol is preferably split into an up-concentration part (with high/"normal" DC) and a gentle actuation with low DC. During the up-concentration part, beads are attracted within short time to a sensor surface. The gentle attraction part of the actuation protocol with the low duty-cycle (typically 2-5%) is diffusion-limited, but a high signal level can be obtained.

While the invention was described above with reference to particular embodiments, various modifications and extensions are possible, for example:
  The sensor device can comprise any suitable sensor to detect the presence of magnetic particles on or near to a sensor surface, based on any property of the particles, e.g. it can detect via magnetic methods (e.g. magnetoresistive, Hall, coils), optical methods (e.g. imaging, fluorescence, chemiluminescence, absorption, scattering, evanescent field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), combinations thereof, etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio) chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink-jet printing on a substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

With nano-particles are meant particles having at least one dimension ranging between 3 nm and 5000 nm, preferably between 10 nm and 3000 nm, more preferred between 50 nm and 1000 nm.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A method for attracting magnetic particles to a contact surface comprising:
    generating a pulsed magnetic field with a duty cycle larger than about 25% to create a "global attraction phase" which concentrates magnetic particles at the contact surface and generating the pulsed magnetic field with the duty cycle smaller than about 10% to create a "local attraction" phase in which the magnetic particles are attracted and diffuse to contact the contact surface.

2. The method according to claim 1, wherein the duty cycle ranges between about 2% and about 5% during the local attraction phase.

3. The method or the sensor device according to claim 1, wherein the global attraction phase precedes the local attraction phase.

4. The method according to claim 1, wherein a frequency of the pulsed magnetic field during the local attraction phase ranges between about 1 Hz and about 4 Hz.

5. The method according to claim 1, wherein the contact surface comprises binding sites for the magnetic particles.

6. The method according to claim 3, further including:
    detecting the magnetic particles at the contact surface during and/or after the local attraction phase.

7. The method according to claim 1, further including:
    detecting the magnetic particles at the contact surface with an optical, magnetic, mechanical, acoustic, thermal, or electrical sensor element.

8. A non-transitory computer-readable medium carrying software configured to control a magnetic field generator to carry out the method according to claim 1.

9. The method according to claim 1, wherein the magnetic particles label molecules and further including:
    detecting the magnetic particles at the contact surface to perform at least one of molecular diagnostics, biological sample analysis, chemical sample analysis, food analysis, and/or forensic analysis.

10. A method of detecting target molecules labeled with magnetic particles comprising:
    pulsing a magnetic field with a duty cycle between about 2% and about 5% to attract the molecules labeled with the magnetic particles to a contact surface; and
    during the pulsing, detecting the molecules labeled with the magnetic particles at the contact surface.

11. The method according to claim 10, further including:
    prior to pulsing the magnetic field with the duty cycle between about 2% and about 5%, pulsing the magnetic field with a duty cycle greater than about 25%.

12. A sensor device for the detection of magnetic particles at a contact surface comprising:
    a) a magnetic field generator configured to generate a magnetic field that attracts magnetic particles to the contact surface;
    b) a controller configured to control the magnetic field generator to generate a pulsed magnetic field with a duty cycle smaller than 10% during a "local attraction phase" to attract the magnetic particles.

13. Use of the sensor device according to claim 12 for molecular diagnostics, biological sample analysis, chemical sample analysis, food analysis, and/or forensic analysis.

14. The sensor device according to claim 12, further including:
    a sensor element configured to detect the magnetic particles at the contact surface during the "local attraction phase".

15. The sensor device according to claim 12, wherein the controller is further configured to control the magnetic field generator to pulse the magnetic field with a duty cycle greater than 25% preceding the "local attraction phase".

16. The sensor device according to claim 15, further including:
    a sensor element configured to detect the magnetic particles at the contact surface during the "local attraction phase".

17. The sensor device according to claim 16, wherein the contact surface includes binding sites for the magnetic particles.

18. The sensor device according to claim 16, wherein the sensor element includes one of an optical, magnetic, mechanical, acoustic, thermal, or electrical sensor element.

19. The sensor device according to claim 15, wherein during the local attraction phase, the controller is configured to control the magnetic field generator to generate magnetic field pulses with a duty cycle between 2% and 5%.

20. The sensor device according to claim 19, wherein the controller is configured to control the magnetic field generator to pulse the magnetic field with a frequency between about 0.2 Hz and about 10 Hz during the "local attraction phase".

\* \* \* \* \*